United States Patent [19]

Sweeney et al.

[11] 4,192,822
[45] Mar. 11, 1980

[54] PROCESS FOR PRODUCING HALOGENATED HYDROCARBONS

[75] Inventors: Richard F. Sweeney, Elma; Bernard F. Sukornick, Williamsville, both of N.Y.

[73] Assignee: Allied Chemical Corporation, Morris Township, Morris County, N.J.

[21] Appl. No.: 8,898

[22] Filed: Feb. 2, 1979

Related U.S. Application Data

[63] Continuation-in-part of Ser. No. 843,759, Oct. 20, 1977, Pat. No. 4,145,368.

[51] Int. Cl.² ............................................. C07C 19/08
[52] U.S. Cl. ................. 260/653; 260/653.8
[58] Field of Search ............... 260/653, 653.8, 658

[56] References Cited

U.S. PATENT DOCUMENTS

| 2,598,411 | 5/1952 | Miller et al. | 260/653 |
| 2,644,845 | 7/1953 | McBee | 260/653 |
| 2,697,124 | 12/1954 | Mantell | 260/653 |
| 3,651,156 | 3/1972 | Scherer et al. | 260/653 |
| 3,697,608 | 10/1972 | Bellis | 260/653.5 |

FOREIGN PATENT DOCUMENTS

2144160  3/1973  Fed. Rep. of Germany.

*Primary Examiner*—C. Davis
*Attorney, Agent, or Firm*—Alan M. Doernberg; Jay P. Friedenson

[57] ABSTRACT

A chlorine-donating perhalogenated hydrocarbon such as fluorocarbon 133a is reacted in the vapor phase with a hydrogen-donating halogenated hydrocarbon such as fluorocarbon 113a in the presence of a catalyst to produce a first halogenated fluorocarbon product with one less chlorine and one more hydrogen than the chlorine donating perhalogenated hydrocarbon and one less hydrogen and one more chlorine than the hydrogen donating halogenated hydrocarbon. Preferred catalysts are activated carbon and especially chromium oxides and oxyfluorides. The products such as fluorocarbon 123 are useful in aerosol, refrigerant and foaming applications, and as intermediates to other chlorofluorocarbons.

13 Claims, No Drawings

PROCESS FOR PRODUCING HALOGENATED HYDROCARBONS

CROSS REFERENCE TO RELATED APPLICATION

This application is a continuation-in-part of copending application Ser. No. 843,759, filed Oct. 20, 1977, now U.S. Pat. No. 4,145,368.

BACKGROUND OF THE INVENTION

The present invention relates to the production of chlorofluorocarbons and especially chlorofluoroethanes having a hydrogen.

Chlorofluorocarbons are now widely used as aerosol propellants, refrigerants and foaming agents. The use of perhalogenated chlorofluorocarbons (having no hydrogens), especially as aerosol propellants, has been questioned because of the asserted possibility of damage to the earth's ozone layer. Non-perhalogenated chlorofluorocarbons have been suggested as "stratospherically safe" propellants because of the likelihood that they would decompose in the lower atmosphere.

Non-perhalogenated chlorofluorocarbons may be prepared in one or more steps involving replacemtn of hydrogens by chlorine or fluorine. Production of the desired non-perhalogenated chlorofluorocarbon is limited, however, by the coproduction of perhalogenated chlorofluorocarbons as byproducts due to the overhalogenation of the starting material. For example, when 1,1,1-trifluoro-2-chloroethane (fluorocarbon 133a according to the ASHRAE designation) is chlorinated with $Cl_2$ by any method, some overchlorinated byproduct, 1,1,1-trifluoro-2,2,2-trichloroethane (fluorocarbon 113a) is produced. In the absence of a separate use for fluorocarbon 113a, this overchlorination detracts from the overall yield of fluorocarbon 123 based upon both hydrocarbon starting material and halogen reactants. It has now been surprisingly found that the fluorocarbon 113a byproduct can be converted to the fluorocarbon 123 product without the introduction of new reactants into the overall process or significant increases in the halogen waste byproduct stream.

The disproportionation of fluorochlorocarbons is well known in the art. The disproportionation reaction involves an exchange of chlorine and fluorine leading to more highly fluorinated compounds and to compounds of lower fluorine but higher chlorine content. In general, complex mixtures are formed since the disproportionation reaction theoretically can be repeated until compounds having only chlorine atoms and fluorine atoms are left in the mixture. In general, the disproportionation usually does not proceed to this ultimate end.

In contrast to prior art disproportionations, the reaction of the subject invention involves a chlorine-hydrogen exchange in which a perhalogenated hydrocarbon such as fluorocarbon 113a gives up a chlorine atom and receives a hydrogen and a halogenated hydrocarbon such as fluorocarbon 133a gives up a hydrogen and receives a chlorine.

BRIEF DESCRIPTION OF THE INVENTION

The present invention includes a process for producing halogenated hydrocarbons of 1 or 2 carbons which comprises reacting a chlorine-donating perhalogenated hydrocarbon selected from the group consisting of carbon tetrachloride, trichloromonofluoromethane, dichlorodifluoromethane, hexachloroethane, pentachloromonofluoroethane, tetrachlorodifluoroethane and trichlorotrifluoroethane with a hydrogen-donating halogenated hydrocarbon selected from the group consisting of trifluoromethane, difluoromethane, methyl fluoride, chlorodifluoromethane, dichloromonofluoromethane, methyl chloride, methylene chloride, chloroform, monochloromonofluoromethane, ethyl chloride, ethyl fluoride, monochloromonofluoroethane, dichloroethane, difluoroethane, trichloroethane, trifluoroethane, monochlorodifluoroethane, dichloromonofluoroethane, tetrachloroethane, trichloromonofluoroethane, dichlorodifluoroethane, monochlorotrifluoroethane and tetrafluoroethane in the presence of a catalyst selected from the group consisting of chromium oxides and oxyfluorides and activated carbon and recovering a first halogenated hydrocarbon product which is said hydrogen-donating halogenated hydrocarbon with one less hydrogen and one more chlorine and a second halogenated hydrocarbon product which is said chlorine-donating perhalogenated hydrocarbon with one more hydrogen and one less chlorine.

DETAILED DESCRIPTION OF THE INVENTION

The chlorine-donating perhalogenated hydrocarbon used in the present process has either one cabon and four halogens (at least two of which are chlorine and the remainder, if any, are fluorine) or has two carbons and six halogens (at least three of which are chlorine and the remainder, if any, are fluorine). Thus suitable perhalomethanes are carbon tetrachloride, trichloromonofluoromethane and dichlorodifluoromethane. Suitable perhaloethanes are hexachloroethane, pentachloromonofluoroethane, tetrachlorodifluoroethane and trichlorotrifluoroethane. While both symmetrical and assymetrical isomers may be used, for tetrachlorodifluoroethane and trichlorotrifluoroethane, the assymetrical isomers (having a $CCl_3$- group) are preferred. Thus the preferred perhaloethanes are of the formula $R-CCl_3$ where R is $CCl_3$, $CCl_2F$, $CClF_2$ or $CF_3$ and the exemplary perhalogenated hydrocarbon used in the examples is $CF_3CCl_3$, called 1,1,1-trichloro-2,2,2-trifluoroethane or fluorocarbon 113a.

The hydrogen-donating halogenated hydrocarbon is either a halomethane with at least one hydrogen (and up to three hydrogens) or a haloethane with at least two hydrogens (and up to five hydrogens). Thus suitable halomethanes are trifluoromethane, difluoromethane, methyl fluoride, chlorodifluoromethane, dichloromonofluoromethane, monochloromonofluoromethane, methyl chloride, methylene chloride and chloroform. Suitable haloethanes are ethyl chloride, ethyl fluoride, monochloromonofluoroethane, dichloroethane, difluoroethane, trichloroethane, trifluoroethane, monochlorodifluoroethane, dichloromonofluoroethane, tetrachloroethane, trichloromonofluoroethane, dichlorodifluoroethane, monochlorotrifluoroethane and tetrafluoroethane. All isomers of these haloethanes may be used, but the preferred haloethanes are of the formula $CF_3CH_2Y$ where Y is H, Cl or F. The advantage of a $CF_3$ group on the non-hydrogen bearing carbon is that it is apparently more stable to dehydrohalogenation compared to groups containing chlorine. It also apparently causes the hydrogen to be more acidic which may be desirable if the mechanism of the reaction involves proton transfer rather than hydrogen radical transfer. The preferred halomethanes are of the formula CH₂XF where X is H, Cl or E. The exemplary hydrogen-donating halogenated hydrocarbon used in the Examples is CF₃CH₂Cl, called 1,1,1-trifluoro-2-chloroethane or fluorocarbon 133a.

In general, it is preferred that the two reactants be selected such that the chlorine-donating perhalogenated hydrocarbon has more chlorine than the hydrogen-donating halogenated hydrocarbon. It is also preferred that the chlorine-donating perhalogenated hydrocarbon be of the formula R-CCl₃ and the hydrogen-donating halogenated hydrocarbon be of the formula CH₂XF or CF₃CH₂Y and especially CF₃CH₂Cl (with R, X and Y being as describe above). The reaction between the exemplary reactants CF₃CCl₃ and CH₃CH₂ Cl is described in our copending application Ser. No. 843,759 and in the Examples that follow.

The process of this invention may be practiced by mixing gaseous hydrogen-donating halogenated hydrocarbon such as fluorocarbon 133a and gaseous chlorine-donating perhalogenated hydrocarbon such as fluorocarbon 133a and passing the gaseous mixture into a tubular reactor heated with a suitable furnace. The tubular reactor is packed with catalyst in a granular form. The gas stream exiting the reactor may be passed through a water scrubber, an aqueous caustic scrubber, or calcium chloride drying tower and then condensed in a receiver cooled in a Dry Ice-acetone bath. The product or products can be recovered by fractional distillation.

In practicing such a process with fluorocarbons 133a and 133a, the best results have been obtained using a $Cr_2O_3$ (Guignet Green) catalyst at 346° C., a 98 sec. contact time, and a 1:1 113a:133a molar ratio. The product mixture consisted of 14% 123, 38% 113a, and 46% 133a based upon chromatographic analysis. The reaction can also be carried out over activated carbon. With activated carbon approximately 5% conversion to 123 was observed at 357° C. Although a small amount of 123 (approximately 1%) was formed over gamma alumina at 301° C., excessive amounts of by-product were formed. Ferric chloride on gamma alumina at 200° C. gave essentially no reaction.

The preferred catalyst for this reaction is $Cr_2O_3$ known as Guignet Green. Other chromium oxide and oxyfluoride catalysts that can be used in this invention are described in U.S. Pat. Nos. 3,258,500; 3,755,477; 3,752,850; 2,271,356; 3,859,424; 3,978,145; 3,651,156 and 3,235,612. It should be appreciated that these catalyst contain chromium at a valence state from three to six and eithe oxide alone or oxide and fluoride.

The catalyst may be used in fixed bed, fluidized bed or spouted bed configuration. Although less preferred, activated carbon is a suitable catalyst for this reaction. Activated carbon can be formed from practically any organic compound capable of being carbonized. Activated carbons prepared from wood, coal, nut shells and petroleum residues are useful. Activated carbon supplied by the Union Carbide Corporation and known as Columbia activated carbon is satisfactory.

The temperature of the reactor should preferably be maintained between about 200° and about 600° C. Below about 200° C. no reaction will take place and above about 600° C. excessive breakdown occurs. The preferred range is between about 300° and about 450° C. with the most preferred range being between about 350° and about 425° C.

Contact time should preferably be between about 1 and about 600 seconds. Longer contact times become noneconomical while shorter times give low conversion. The more preferred contact time is between about 30 and about 120 seconds, with the most preferred contact time being between about 60 and about 110 seconds.

The reaction may be operated at substantially atmospheric pressure or under superatmospheric pressure. The net effect of increased pressure is to increase conversion per cubic foot of catalyst per unit time and is not critical to the process.

The molar ratio of the two reactants is preferably about 1.1. No advantage accrues to using a molar excess of either reactant.

EXAMPLE 1

Catalyst Preparation

A 1 inch inside diameter 27 inch long Inconel pipe was packed with 275 cc Guignet Green $Cr_2O_3$ 6–10 mesh (American Standard) chips. The catalyst was conditioned by drying under nitrogen at 180° C. for 24 hours then for an additional 24 hours at 300° C. An $N_2$/HF gas stream was then passed over the catalyst at 300° C. for 24 hours. This treatment with HF is not essential in preparing catalyst for use in the process of this invention.

EXAMPLE 2

Reaction of Fluorocarbon 133a and Fluorocarbon 113a Over $Cr_2O_3$ 113a and 133a were passed into the reactor described in Example 1 at 346° C., each at a rate of 0.1 moles/hour, for a total of 1 hour (80 seconds contact time). Of 31.5 gm of organic feed, 25.5 gm were recovered representing an 81% organic recovery. Gas chromatography analysis of the recovered organic material indicated that the recovered organic mixture was 46.5% of 133a, 33.9% of 113a, and 14.1% of 123, by area.

EXAMPLE 3

Reaction Over $Cr_2O_3$ at Higher Temperature 113a at 0.12 moles/hour and 133a at 0.13 moles/hour were passed into the reactor described in Example 1 at 376° C. for 1 hour (80 seconds contact time). The product mixture was determined by gas chromatography analysis to be 42.4% of 133a, 44.6% of 113a, and 12.0% of 123, by area.

COMPARATIVE EXAMPLE 4

Empty Tube 113a fed at a rate of 0.32 moles/hour and 133a fed at a rate of 0.32 moles/hour were passed into the unpacked Inconel reactor of Example 1 maintained at 350° C. Essentially no conversion to 123 product was observed.

EXAMPLE 5

Activated Carbon

The Inconel reactor of Example 1 was packed with activated carbon and maintained at 350° C. 113a and 133a were passed in, each at a rate of 0.12 moles/hour, for a total of 1 hour (contact time 91 seconds). The product mixture was determined by gas chromatography to be 48.0% of 133a, 46.6% of 133a and 4.8% of 123, by area.

COMPARATIVE EXAMPLE 6

Alumina

The reactor of Example 1 was charged with 275 cc of activated gamma alumina. The catalyst was maintained at 300° C. for 16 hours under helium purge. 113a and 133a were then passed into the reactor maintained at 301° C., each at a rate of 0.27 moles/hour. The product mixture was determined by gas chromatography to be 61.4% of 113a, 27.2% of 133a, and 1.0% of 123, and 10.3% other products, by area.

COMPARATIVE EXAMPLE 7

FeCl₃ on Gamma Alumina

The catalyst was prepared by soaking 500 gm of Girdler T-74 gamma alumina in an aqueous solution of 120 gm of $FeCl_3$. The mixture was dryed under vacuum at between 45° and 90° C. 275 ml of this catalyst was packed into the reactor tube of Example 1 and heated under helium purge at 150°–250° C. for 48 hours.

133a and 113a were passed into the reactor at 200° C., each at a rate of 0.20 moles/hour. Gas chromatography analysis of the product mixture showed 52.0% of 113a, 47.8% of 133a and no significant conversion to G-123.

We claim:

1. A process for producing halogenated hydrocarbons of 1 or 2 carbons which comprises reacting a chlorine-donating perhalogenated hydrocarbon selected from the group consisting of carbon tetrachloride, trichloromonofluoromethane, dichlorodifluoromethane, hexachloroethane, pentachloromonofluoroethane, tetrachlorodifluoroethane and trichlorotrifluoroethane with a hydrogen-donating halogenated hydrocarbon selected from the group consisting of trifluoromethane, difluoromethane, methyl fluoride, chlorodifluoromethane, dichloromonofluoromethane, methyl chloride, methylene chloride, chloroform, monochloromonofluoromethane, ethyl chloride, ethyl fluoride, monochloromonofluoroethane, dichloroethane, difluoroethane, trichloroethane, trifluoroethane, monochlorodifluoroethane, dichloromonofluoroethane, tetrachloroethane, trichloromonofluoroethane, dichlorodifluoroethane, monochlorotrifluoroethane and tetrafluoroethane in the presence of a catalyst selected from the group consisting of chromium oxides and oxyfluorides and activated carbon and recovering a first halogenated hydrocarbon product which is said hydrogen-donating halogenated hydrocarbon with one less hydrogen and one more chlorine and a second halogenated hydrocarbon product which is said chlorine-donating perhalogenated hydrocarbon with one more hydrogen and one less chlorine.

2. The process of claim 1 wherein said chlorine-donating perhalogenated hydrocarbon has more chlorines than does said hydrogen-donating halogenated hydrocarbon.

3. The process of claim 1 wherein said chlorine-donating perhalogenated hydrocarbon has two carbons.

4. The process of claim 1 wherein said chlorine-donating perhalogenated hydrocarbon is of the formula $R-CCl_3$ where R is Cl, F, $CCl_3$, $CCl_2F$, $CClF_2$ or $CF_3$.

5. The process of claim 4 wherein said chlorine-donating perhalogenated hydrocarbon is $CF_3CCl_3$.

6. The process of claim 1 wherein said hydrogen-donating halogenated hydrocarbon has two carbons.

7. The process of claim 1 wherein said hydrogen-donating halogenated hydrocarbon is of the formula $CH_2XF$ with X being H, Cl or F or of the formula $CF_3CH_2Y$ with Y being H, Cl or F.

8. The process of claim 7 wherein said halogen-donating halogenated hydrocarbon is $CF_3CH_3$.

9. The process of claim 8 wherein said chlorine-donating perhalogenated hydrocarbon is of the formula $R-CCl_3$ where R is Cl, F, $CCl_3$, $CCl_2F$, $CClF_2$ or $CF_3$.

10. The process of claim 7 wherein said chlorine-donating perhalogenated hydrocarbon is of the formula $R-CCl_3$ wherein R is Cl, F, $CCl_3$, $CCl_2F$, $CClF_2$ or $CF_3$.

11. The process of claim 1 wherein said catalyst is a chromium oxide.

12. The process of claim 11 wherein said chromium oxide catalyst is $Cr_2O_3$.

13. The process of claim 1 conducted at between about 200° C. and about 600° C. with a catalyst contact time between about 1 and 600 seconds.

* * * * *